(12) United States Patent
May et al.

(10) Patent No.: US 7,673,531 B2
(45) Date of Patent: Mar. 9, 2010

(54) MULTIVOLUME PIPETTE

(75) Inventors: Yves Andre May, Versailles (FR);
Bernard Henri Julien Roussel, Bondy (FR); Frederic Millet, Paris (FR)

(73) Assignee: Gilson S.A.S., Villiers-le-Bel (FR)

( * ) Notice: Subject to any disclaimer, the term of this patent is extended or adjusted under 35 U.S.C. 154(b) by 522 days.

(21) Appl. No.: 11/619,882

(22) Filed: Jan. 4, 2007

(65) Prior Publication Data
US 2007/0169571 A1    Jul. 26, 2007

(30) Foreign Application Priority Data
Jan. 6, 2006    (FR)    .................................. 06 00134

(51) Int. Cl.
*B01L 3/021* (2006.01)
(52) U.S. Cl. .................................. 73/864.16
(58) Field of Classification Search .................. None
See application file for complete search history.

(56) References Cited
U.S. PATENT DOCUMENTS

| 3,193,148 | A |   | 7/1965  | Anthon           |         |
|-----------|---|---|---------|------------------|---------|
| 3,640,434 | A | * | 2/1972  | Walker           | 222/144.5 |
| 3,835,874 | A |   | 9/1974  | Dellasala        |         |
| 4,554,939 | A |   | 11/1985 | Kern et al.      |         |
| 4,679,446 | A |   | 7/1987  | Sheehan et al.   |         |
| 5,540,562 | A | * | 7/1996  | Giter            | 417/254 |
| 2005/0220676 | A1 |   | 10/2005 | Tran          |         |

OTHER PUBLICATIONS

French Search Report for French Patent Application No. 06 00134, mailed Sep. 1, 2006.

* cited by examiner

*Primary Examiner*—Robert R Raevis
(74) *Attorney, Agent, or Firm*—Foley & Lardner LLP

(57) ABSTRACT

A multivolume pipette is provided. In an exemplary embodiment, the multivolume pipette includes a pipette body, a piston disposed within the pipette body, a first chamber, a second chamber, and a valve. The first chamber and the second chamber are defined at least in part by an inner wall of the pipette body and the piston. The valve is capable of placing the second chamber in fluid communication with an external environment to provide a first volume range of the multivolume pipette. The valve is also capable of placing the second chamber in fluid communication with the first chamber to provide a second volume range of the multivolume pipette.

28 Claims, 3 Drawing Sheets

MULTIVOLUME PIPETTE

FIELD

The subject of the disclosure relates generally to a multivolume pipette for aspirating and dispensing a fluid. More specifically, the disclosure relates to a multi-chamber pipette in which a volume range is controlled by one or more valves in fluid communication with an external environment.

BACKGROUND

Conventional pipettes generally include a cylindrical body, a cylindrical piston within a cavity of the cylindrical body, and a mechanical or automated actuating mechanism for actuating the cylindrical piston. When the actuating mechanism causes the cylindrical piston to perform an upward stroke, liquid is aspirated into a pipette tip attached to the end of the cylindrical body. When the actuating mechanism causes the cylindrical piston to perform a downward stroke, liquid is dispensed from the pipette tip. The diameter of the cavity and the diameter of the piston define a volume range for the pipette. The volume range can refer to the range of volumes which the pipette is able to reliably aspirate and dispense. In general, large diameters correspond to a large volume range and small diameters correspond to a small volume range. For example, a cylindrical pipette in which the cavity and the piston have a relatively small diameter may have a volume range of 1-10 μL. A cylindrical pipette in which the cavity and the piston have a larger diameter may have a volume range of 100-1000 μL. Because of their uniform nature, conventional cylindrical pipettes can only aspirate and dispense within a single volume range.

A multivolume pipette is a pipette which is capable of reliably operating over more than one volume range. U.S. Pat. No. 4,679,446 describes a multivolume pipette in which the cavity of the pipette body is composed of sections, each of which has a distinct diameter. The multivolume pipette also includes a piston which is composed of sections with distinct diameters. A seal surrounds each piston section to form a plurality of chambers within the cavity. Each chamber includes a channel opening which is in fluid communication with an outside environment when no pipette tip is installed on the pipette body. As such, this multivolume pipette requires pipette tips of varying sizes to control the volume range of the pipette.

For example, a first pipette tip may cover only the bottommost channel opening such that the bottommost channel opening is no longer in communication with the outside environment. As such, the bottommost chamber is able to build pressure and is an operational pipette chamber. The other chambers are not able to build pressure because they are still in fluid communication with the outside environment. Thus, the multivolume pipette can operate within a first volume range corresponding to the bottommost chamber. A second (larger) pipette tip may cover the bottommost channel opening and the next successive channel opening such that the first two chambers become operational chambers. As such, the second pipette tip causes the pipette to operate in a second volume range, where the second volume range is larger than the first volume range. A third pipette tip can be used to provide a third volume range, and so on. In addition to requiring specially tailored pipette tips, this multivolume pipette is also limited because it does not provide any mechanism to ensure that a user selects the proper pipette tip.

U.S. Pat. No. 3,640,434 describes another multivolume pipette in which the piston and the cavity are each composed of sections of increasing diameter. The chambers formed by the piston and the cavity have channel openings which are in fluid communication with an annular space within the pipette body. A user of the pipette can rotate a ring to cause an elliptical seal to move inside the annular space such that the chambers can be placed into or out of communication with one another to control the volume range of the pipette. For example, positioning the elliptical seal such that only the bottommost chamber is in communication with the annular space corresponds to a first volume range. Positioning the elliptical seal such that the two bottommost chambers are in communication with the annular space corresponds to a second (larger) volume range, and so on. This multivolume pipette is limited in part because of the high risk of user error involved in manually placing the elliptical seal. Further, the elliptical seal is subject to wear and tear as it is repeatedly moved along the cavity. A deformed or otherwise damaged elliptical seal can impair the ability to isolate cavities from one another and lead to inaccurate volume transfers. In addition, this multivolume pipette requires at least two operations by the user to perform a volume transfer. The user must adjust the elliptical seal to obtain the proper volume range and also set the piston stroke to obtain the correct volume within that volume range.

Thus, there is a need for a multivolume pipette which is capable of operating in all volume ranges with a single pipette tip. There is also a need for a multivolume pipette in which the risk of operator error is minimized. Further, there is a need for a multivolume pipette in which a specific volume in a specific volume range can be selected by a single user action.

SUMMARY

A multivolume pipette is provided. In an exemplary embodiment, the multivolume pipette includes a pipette body, a piston disposed within the pipette body, a first chamber, a second chamber, and a valve. The first chamber and the second chamber are defined at least in part by an inner wall of the pipette body and the piston. The valve is capable of placing the second chamber in fluid communication with an external environment to provide a first volume range of the multivolume pipette. The valve is also capable of placing the second chamber in fluid communication with the first chamber to provide a second volume range of the multivolume pipette.

In another exemplary embodiment, the multivolume pipette includes a control module capable of controlling the valve. The control module can be incorporated within the multivolume pipette or a standalone controller to which the multivolume pipette is attached, depending on the embodiment. The control module can include a volume selector which a user can use to select a desired volume. In an exemplary embodiment, the control module can automatically control the valve based on the desired volume. The control module can also automatically control a stroke of the piston based on the desired volume. The control module can also include an indicator for indicating whether the multivolume pipette is operating in the first volume range or the second volume range. In one embodiment, the control module further comprises an override such that the user can manually control the valve.

A method for adjusting a volume capacity of a pipette is also provided. The method includes receiving a requested volume from a user and determining a volume range within which the received requested volume falls. If the determined volume range is a first volume range, a valve is used to place a second chamber of the pipette in fluid communication with an external environment. The second chamber is defined at least in part by an inner wall of a pipette body and a piston. If the determined volume range is in a second volume range, first valve may be used to place the second chamber in fluid communication with a first chamber of the pipette. The first chamber is also defined at least in part by the inner wall of the pipette body and the piston.

Other principal features and advantages will become apparent to those skilled in the art upon review of the following drawings, the detailed description, and the appended claims.

BRIEF DESCRIPTION OF THE DRAWINGS

Exemplary embodiments will hereafter be described with reference to the accompanying drawings wherein like numerals denote like elements.

DETAILED DESCRIPTION

Figure 1:
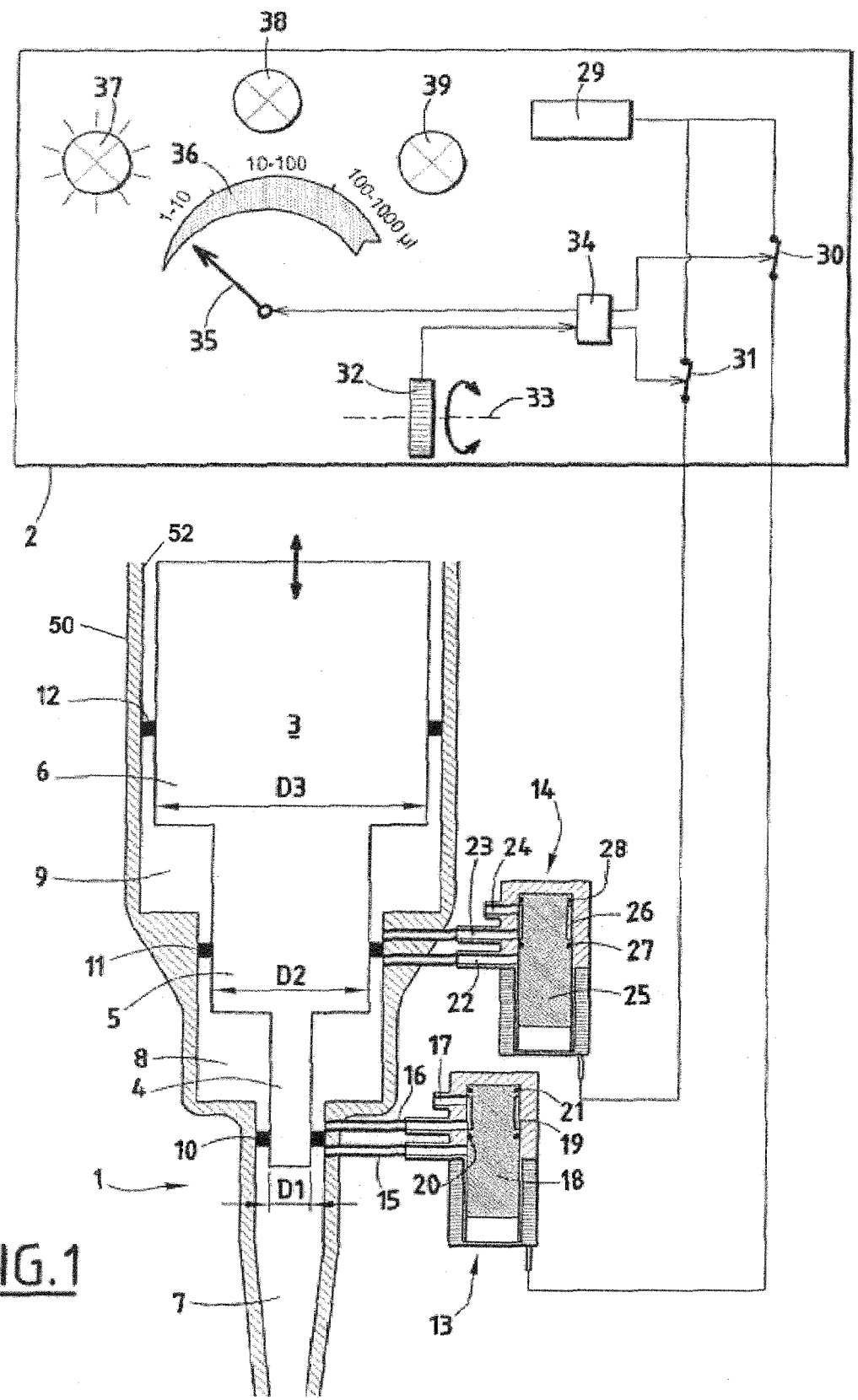
FIG. 1 is a cross-sectional view of a multivolume pipette configured to pipette within a first volume range in accordance with an exemplary embodiment.

FIG. 1 is a cross-sectional view of a multivolume pipette 1 and a control module 2 in accordance with an exemplary embodiment. In an exemplary embodiment, control module 2 can be incorporated within multivolume pipette 1. Alternatively, control module 2 can be an external controller to which multivolume pipette 1 is connected. Multivolume pipette 1 includes a piston 3 enclosed within a pipette body 50. Piston 3 can be actuated automatically or manually by a user depending on the embodiment. Piston 3 has a first section 4, a second section 5, and a third section 6. First section 4 has a diameter D1, second section 5 has a diameter D2 which is larger than D1, and third section 6 has a diameter D3 which is larger than D2. In an alternative embodiment, piston can have any number of sections including two, four, five, etc. In another alternative embodiment, the piston sections can be of any diameter.

A first chamber 7 of multivolume pipette 1 is defined by an inner wall 52 of pipette body 50, piston 3, and a first seal 10 surrounding a portion of first section 4. A second chamber 8 is defined by inner wall 52, piston 3, first seal 10, and a second seal 11 surrounding a portion of second section 5. A third chamber 9 is defined by inner wall 52, piston 3, second seal 11, and a third seal 12 surrounding a portion of third section 6. In an exemplary embodiment, a first volume range for multivolume pipette 1 can be provided by ensuring that only first chamber 7 is able to build pressure during aspiration and dispensing. A second volume range for multivolume pipette 1 can be provided by placing second chamber 8 in fluid communication with first chamber 7 such that pressure can be built within both first chamber 7 and second chamber 8. A third volume range can be provided by placing second chamber 8 in fluid communication with first chamber 7, and third chamber 9 in fluid communication with second chamber 8 such that pressure can be built within all three chambers. In an alternative embodiment, multivolume pipette can include any number of chambers.

A first valve 13 and a second valve 14 can be used to control whether first chamber 7, second chamber 8, and/or third chamber 9 are in communication with one another. First valve 13 and second valve 14 can be any valve or other device capable of controlling which chambers are in fluid communication with one another. In an exemplary embodiment, first valve 13 and second valve 14 can be electrical valves capable of being automatically controlled by control module 2. In another exemplary embodiment, first valve 13 and/or second valve 14 can be an LHDA 053 1115H valve sold by LEE COMPANY. In one embodiment, first valve 13 and second valve 14 can be approximately one centimeter by two centimeters in size. Further, first valve 13 and second valve 14 can be placed within or external to pipette body 50 depending on the embodiment.

First valve 13 includes a first channel 15 in fluid communication with first chamber 7, a second channel 16 in fluid communication with second chamber 8, and a third channel 17 in fluid communication with an external environment. First valve 13 also includes a channel connector 18 which can be moved to control communication among first channel 15, second channel 16, and third channel 17. Channel connector 18 includes an annular recess 19 surrounded by a first O-ring 20 and a second O-ring 21. As illustrated with reference to FIG. 1, channel connector 18 is positioned such that annular recess 19 provides fluid communication between second channel 16 and third channel 17. As such, second chamber 8 is in fluid communication with the external environment and first chamber 7 is isolated from second chamber 8.

Second valve 14 can be the same as first valve 13 or different, depending on the embodiment. Second valve 14 includes a first channel 22 in communication with second chamber 8, a second channel 23 in communication with third chamber 9, and a third channel 24 in communication with the external environment. Second valve 14 also includes a channel connector 25 which can be moved to control communication among first channel 22, second channel 23, and third channel 24. Channel connector 25 includes an annular recess 26 surrounded by a first O-ring 27 and a second O-ring 28.

As illustrated with reference to FIG. 1, channel connector 25 is positioned such that annular recess 26 provides fluid communication between second channel 23 and third channel 24. As such, third chamber 9 is in fluid communication with the external environment, and only first chamber 7 is operational for aspirating and dispensing. In an exemplary embodiment, operating only first chamber 7 can provide a first volume range of multivolume pipette 1. Operating first chamber 7 and second chamber 8 can provide a second volume range of multivolume pipette 1. Similarly, operating first chamber 7, second chamber 8, and third chamber 9 can provide a third volume range of multivolume pipette 1. In an exemplary embodiment, the first volume range can be a first decade, the second volume range can be a second decade, and the third volume range can be a third decade. For example, the first volume range can be approximately 1-10 μL, the second volume range can be approximately 10-100 μL, and the third volume range can be approximately 100-1000 μL. Alternatively, the volume ranges can cover any range of volumes, the volume ranges can be discontinuous, and/or the volume ranges can overlap one another.

Control module 2 includes a power supply 29 which is capable of supplying power to first valve 13 when a switch 30 is in a closed position and second valve 14 when a switch 31 is in a closed position. Control module also includes a volume selector 32 which a user can use to select a volume that he/she desires to pipette. In an exemplary embodiment, volume selector 32 can be a thumbwheel which the user rotates about an axis 33. Alternatively, volume selector can be any button, switch, or other mechanism which a user can use to select a desired volume. Volume selector 32 can be in communication with a volume controller 34. Volume controller 34 can use an input from volume selector 32 to control switch 30 and switch 31. in an exemplary embodiment, volume controller 34 can automatically control switch 30 and switch 31 such that first valve 13 and second valve 14 are properly positioned for the selected volume. Volume controller 34 can also control a stroke of piston 3 such that the selected volume can be aspirated and dispensed. As such, the user can use multivolume pipette 1 to transfer a desired volume by performing a single operation. Volume controller 34 can also use an input from volume selector 32 to control a needle 35 for indicating a selected volume on a display 36. In an alternative embodiment, the selected volume can be indicated on a digital display or by any other method known to those of skill in the art. As illustrated with reference to FIG. 1, needle 35 and display 36 indicate that the selected volume is approximately three µL.

Control module 2 also includes a first indicator 37, a second indicator 38, and a third indicator 39. In an exemplary embodiment, first indicator 37 can indicate when the selected volume falls within the first volume range, second indicator 38 can indicate when the selected volume falls within the second volume range, and third indicator 39 can indicate when the selected volume falls within the third volume range. As illustrated with reference to FIG. 1, first indicator 37 is lit up to indicate that the selected volume falls within the first volume range. In an exemplary embodiment, first indicator 37, second indicator 38, and third indicator 39 can be different colors to help prevent user error. The different colors can correspond to colors of pipette tips (or pipette tip packaging) which can be used for the various volume ranges. For example, first indicator 37 and pipette tips used to pipette within the first volume range can both be red, second indicator 38 and pipette tips used to pipette within the second volume range can both be green, etc. In an alternative embodiment, first indicator, second indicator, and third indicator can be the same color. Alternatively, a single indicator such as a multi-color LED can be used to indicate the volume range. Alternatively, a digital display or any other mechanism known to those of skill in the art can be used to indicate the volume range. In another alternative embodiment, indicators may not be included, and the same pipette tip can be used for all operations performed with multivolume pipette 1.

Figure 2:
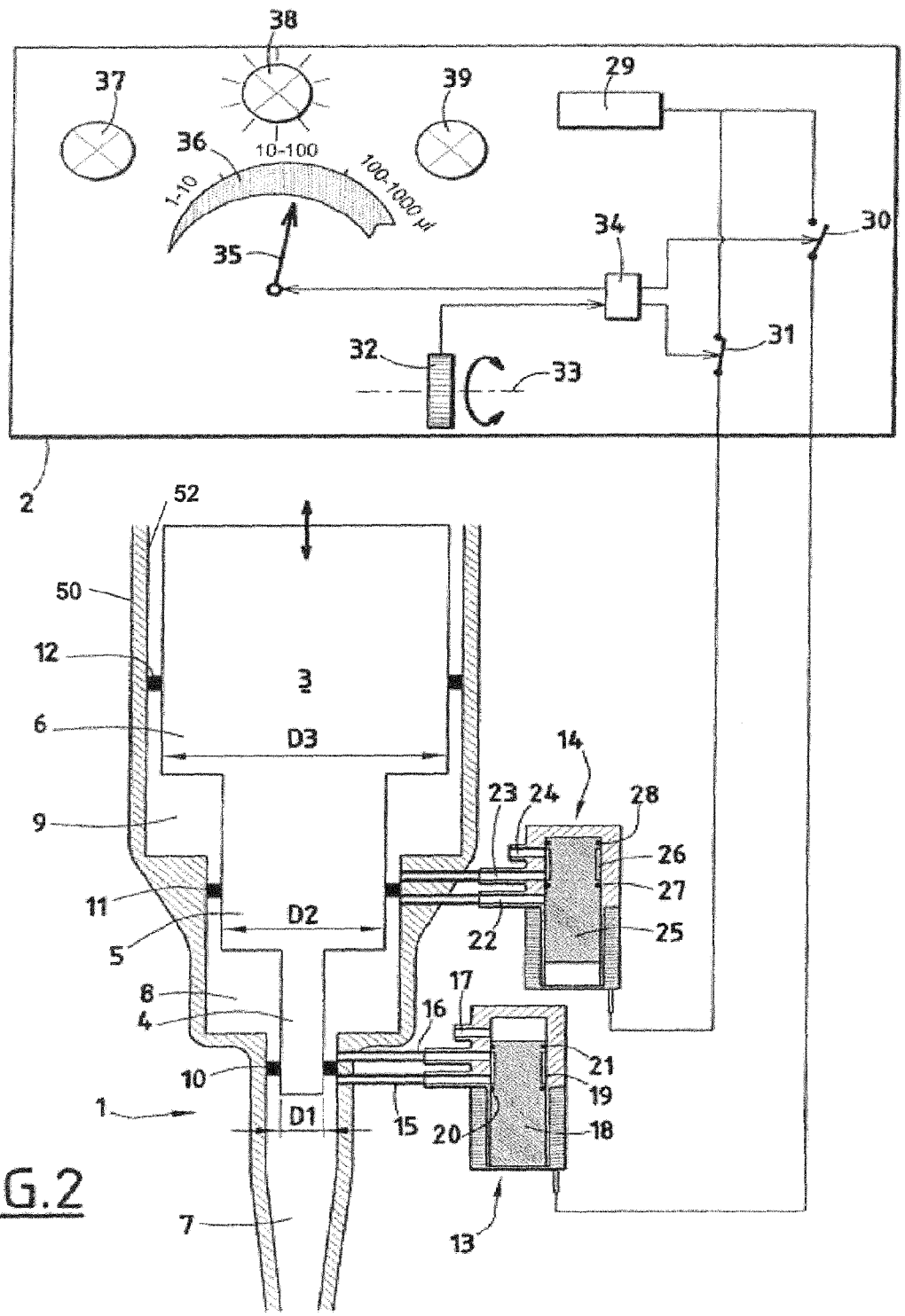
FIG. 2 is a cross-sectional view of the multivolume pipette configured to pipette within a second volume range in accordance with an exemplary embodiment.

FIG. 2 is a cross-sectional view of multivolume pipette 1 configured to pipette within the second volume range in accordance with an exemplary embodiment. Volume selector 32 has been used to select a volume of approximately sixty µL, as indicated by needle 35 and display 36. In addition, second indicator 38 is lit up to indicate that the selected volume falls within the second volume range. Volume controller 34 has opened switch 30 to control channel connector 18 of first valve 13. Channel connector 18 is positioned such that annular recess 19 provides fluid communication between first channel 15 and second channel 16. As such, first chamber 7 is in fluid communication with second chamber 8. Because switch 31 remains in a closed position, third chamber 9 is still in fluid communication with the external environment. As such, first chamber 7 and second chamber 8 are operational such that the second volume range is provided.

Figure 3:
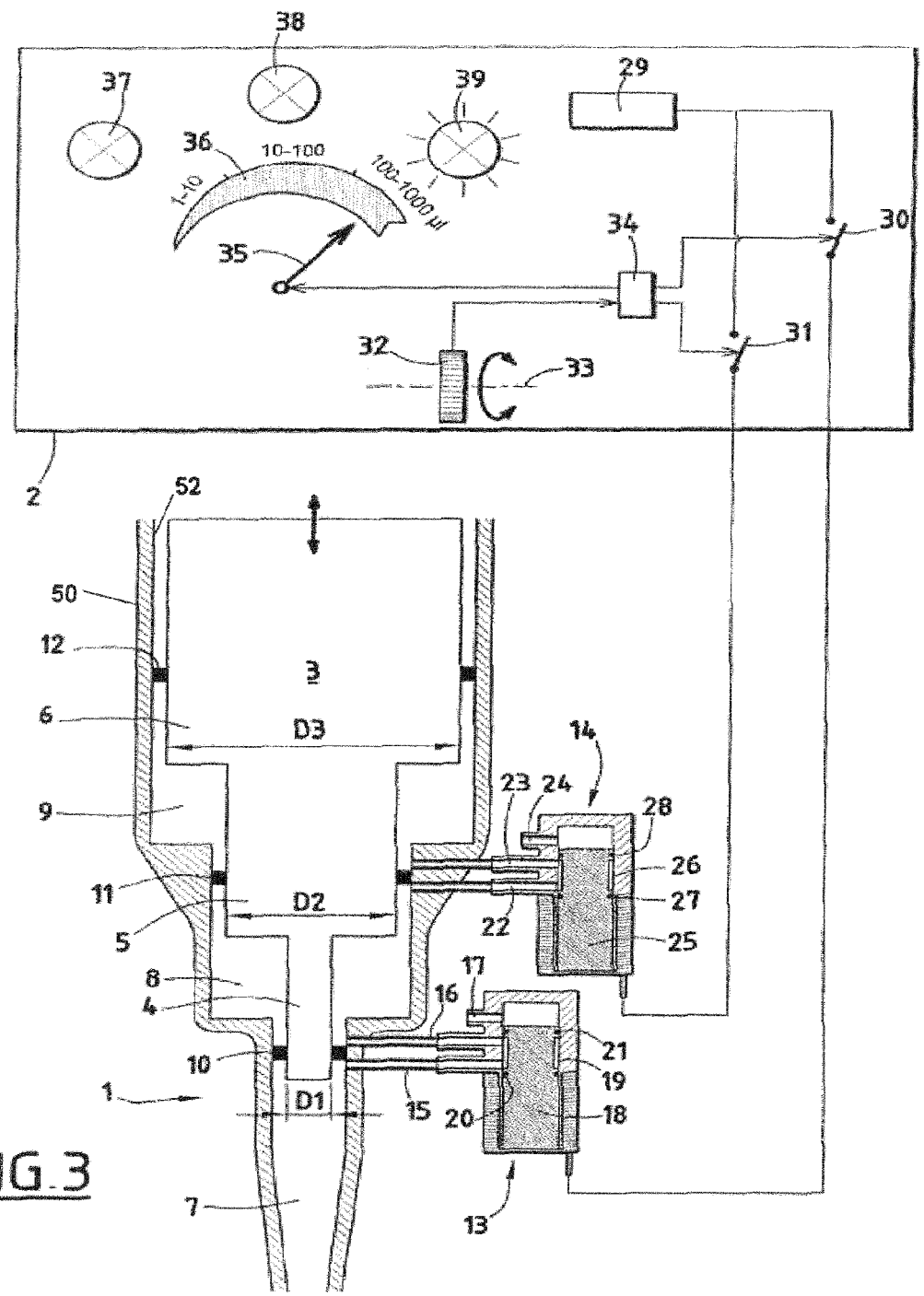
FIG. 3 is a cross-sectional view of the multivolume pipette configured to pipette within a third volume range in accordance with an exemplary embodiment.

FIG. 3 is a cross-sectional view of multivolume pipette 1 configured to pipette within the third volume range in accordance with an exemplary embodiment. Volume selector 32 has been used to select a volume of approximately seven hundred µL, as indicated by needle 35 and display 36. In addition, third indicator 39 is lit up to indicate that the selected volume falls within the third volume range. Volume controller 34 has opened switch 30 to control channel connector 18 of first valve 13. Channel connector 18 is positioned such that annular recess 19 provides fluid communication between first channel 15 and second channel 16. As such, first chamber 7 is in fluid communication with second chamber 8. Volume controller 34 has also opened switch 31 to control channel connector 25 of second valve 14. Channel connector 25 is positioned such that annular recess 26 provides fluid communication between first channel 22 and second channel 23. As such, second chamber 8 is in fluid communication with third chamber 9. Thus, first chamber 7, second chamber 8, and third chamber 9 are all operational such that the third volume range is provided.

In an exemplary embodiment, if the selected volume corresponds to a limit between adjacent volume ranges, multivolume pipette 1 can automatically utilize the smaller volume range to maximize precision. For example, the second volume range can be 10-100 µL and the third volume range can be 100-1000 µL. The user can use volume selector 32 to select a volume of 100 µL. In such a case, volume controller 34 can automatically control first valve 13 and second valve 14 such that multivolume pipette 1 operates in the second volume range (as illustrated with reference to FIG. 2), and not the third volume range.

During a series of volume transfers, precision can be increased by performing each volume transfer within the same volume range. For example, a first experiment can require a series of volume transfers ranging from 70-110 µL, a second experiment can require a series of volume transfers ranging from 90-150 µL, etc. In one embodiment, the user can be allowed to manually override volume controller 34 to control first valve 13 and/or second valve 14. Also, adjacent volume ranges can overlap one another. For example, the first volume range can be approximately 1-11 µL, the second volume range can be approximately 9-110 µL, and the third volume range can be approximately 90-1000 µL. As such, the user can manually control multivolume pipette 1 such that each volume transfer during the first experiment is performed within the second volume range. Similarly, the user can manually control multivolume pipette 1 such that each volume transfer during the second experiment is performed within the third volume range. In an alternative embodiment, the user can override volume controller 34 and manually control the volume range at any time. Alternatively, multivolume pipette 1 may not have control mechanism 34, and first valve 13 and second valve 14 can be manually controlled by the user.

The exemplary embodiments described with reference to FIGS. 1-3 are meant to be non-limiting examples. In alternative embodiments, multivolume pipette can provide any number of volume ranges. For example, multivolume pipette can include four piston sections, four seals, four chambers, and three valves such that four volume ranges can be provided. Alternatively, multivolume pipe e can provide n volume ranges and include n-1 valves. Further, the valves can be replaced by any other valve or device capable of controlling communication among the chambers.

The foregoing description of exemplary embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A multivolume pipette comprising:
a pipette body comprising an inner wall;
a piston disposed within the pipette body;
a first chamber defined at least in part by the inner wall and the piston;
a second chamber defined at least in part by the inner wall and the piston; and
an electrically controlled valve configured to place the second chamber in fluid communication with an external environment to provide a first volume range and to place the second chamber in fluid communication with the first chamber to provide a second volume range.

2. The multivolume pipette of claim 1, wherein the piston comprises a first section with a first diameter and a second section with a second diameter, and further wherein the first diameter is smaller than the second diameter.

3. The multivolume pipette of claim 1, wherein the piston comprises a first section with a first diameter and a second section with a second diameter, and further wherein the first diameter is greater than the second diameter.

4. The multivolume pipette of claim 1, wherein the piston comprises a first section with a first diameter and a second section with a second diameter, and further wherein the first diameter is approximately equal to the second diameter.

5. The multivolume pipette of claim 1, further comprising a third chamber defined at least in part by the inner wall and the piston.

6. The multivolume pipette of claim 5, further comprising a second electrically controlled valve configured to place the third chamber in fluid communication with the second chamber to provide a third volume range.

7. The multivolume pipette of claim 1, wherein the first volume range and the second volume range overlap one another.

8. The multivolume pipette of claim 1, wherein the electrically controlled valve further comprises a first channel in fluid communication with the first chamber, a second channel in fluid communication with the second chamber, and a third channel in fluid communication with the external environment.

9. The multivolume pipette of claim 8, wherein the valve further comprises a channel connector, and further wherein the electrically controlled valve positions the channel connector in a first position to place the second chamber in fluid communication with the external environment by placing the second channel in fluid communication with the third channel.

10. The multivolume pipette of claim 9, wherein the electrically controlled valve positions the channel connector in a second position to place the second chamber in fluid communication with the first chamber by placing the second channel in fluid communication with the first channel.

11. The multivolume pipette of claim 8, wherein the first chamber is further defined by a first seal which surrounds at least a portion of a first section of the piston and further wherein the first channel communicates with the first chamber at a first location on a first side of the first seal.

12. The multivolume pipette of claim 11, wherein the second chamber is further defined by the first seal and a second seal which surrounds at least a portion of a second section of the piston.

13. The multivolume pipette of claim 12, wherein the second channel communicates with the second chamber at a second location on a second side of the first seal, the second side opposite the first side.

14. The multivolume pipette of claim 1, wherein the first volume range is approximately one microliter ($\mu$L) to approximately ten $\mu$L.

15. A multivolume pipette comprising:
a pipette body comprising an inner wall;
a piston disposed within the pipette body;
a first chamber defined at least in part by the inner wall and the piston;
a second chamber defined at least in part by the inner wall and the piston;
an electrically controlled valve configured to place the second chamber in fluid communication with an external environment to provide a first volume range and to place the second chamber in fluid communication with the first chamber to provide a second volume range; and
a control module configured to control the electrically controlled valve based on a selected volume.

16. The multivolume pipette of claim 15, wherein the control module comprises a volume selector which a user can use to select the selected volume.

17. The multivolume pipette of claim 15, wherein the control module is further configured to control a stroke of the piston based on the selected volume.

18. The multivolume pipette of claim 15, wherein the control module comprises an indicator for indicating whether the multivolume pipette is operating in the first volume range or in the second volume range.

19. The multivolume pipette of claim 15, wherein the control module is mounted to the pipette body.

20. The multivolume pipette of claim 15, wherein the control module further comprises an override such that a user can manually control the electrically controlled valve.

21. The multivolume pipette of claim 15, wherein the electrically controlled valve comprises a first channel in fluid communication with the first chamber, a second channel in fluid communication with the second chamber, and a third channel in fluid communication with the external environment.

22. The multivolume pipette of claim 21, wherein the electrically controlled valve further comprises a channel connector, and further wherein the control module controls the electrically controlled valve by causing the electrically controlled valve to move the channel connector to a first position in which the second chamber is in fluid communication with the third channel.

23. The multivolume pipette of claim 21, wherein the electrically controlled valve is configured to move the channel connector between a first position in which the first channel is in fluid communication with the second channel and not the third channel and a second position in which the third channel is in fluid communication with the second channel and not the first channel.

24. The multivolume pipette of claim 21, wherein the electrically controlled valve further comprises a channel connector, and further wherein the control module controls the electrically controlled valve by causing the electrically controlled valve to move the channel connector to a second position in which the second chamber is in fluid communication with the first channel.

25. A method of adjusting a volume capacity of a pipette, the method comprising:
receiving a requested volume from a user in a control module;
determining, in the control module, a volume range within which the received requested volume falls; and controlling, by the control module, an electrically controlled valve to place a second chamber in fluid communication with an external environment if the volume range is in a first volume range, wherein the second chamber is defined at least in part by an inner wall of a pipette body and a piston.

26. The method of claim 25, wherein the electrically controlled valve comprises a channel connector, a second channel in fluid communication with the second chamber, and a third channel in fluid communication with the external environment, and further wherein placing the second chamber in fluid communication with the external environment comprises moving the channel connector such that the second channel is in fluid communication with the third channel.

27. The method of claim 26, further comprising controlling the electrically controlled valve to place the second chamber in fluid communication with a first chamber if the volume range is in a second volume range, wherein the first chamber is defined at least in part by the inner wall and the piston.

28. The method of claim 27, wherein the electrically controlled valve further comprises a first channel in fluid communication with the first chamber, and further wherein placing the second chamber in fluid communication with the first chamber comprises moving the channel connector such that the second channel is in fluid communication with the first channel.

\* \* \* \* \*